(12) United States Patent
Ishii et al.

(10) Patent No.: US 6,800,153 B2
(45) Date of Patent: Oct. 5, 2004

(54) METHOD FOR PRODUCING β-TITANIUM ALLOY WIRE

(75) Inventors: Naoki Ishii, Kanagawa (JP); Takashi Kaneko, Kanagawa (JP); Shin Sumimoto, Hyogo (JP); Hideki Yamamoto, Hyogo (JP); Ichiro Nagao, Hyogo (JP)

(73) Assignees: Terumo Corporation, Tokyo (JP); Tokusen Kogyo Co., Ltd., Hyogo (JP)

( * ) Notice: Subject to any disclaimer, the term of this patent is extended or adjusted under 35 U.S.C. 154(b) by 0 days.

(21) Appl. No.: 10/120,716

(22) Filed: Apr. 11, 2002

(65) Prior Publication Data

US 2002/0174922 A1 Nov. 28, 2002

Related U.S. Application Data

(62) Division of application No. 09/655,949, filed on Sep. 6, 2000, now Pat. No. 6,402,859.

(30) Foreign Application Priority Data

| Sep. 10, 1999 | (JP) | ............................................ 11-256625 |
| Sep. 20, 1999 | (JP) | ............................................ 11-264743 |
| Oct. 5, 1999 | (JP) | ............................................ 11-284006 |

(51) Int. Cl.$^7$ ................................................ C22F 1/18
(52) U.S. Cl. ........................ 148/671; 148/670; 148/687; 148/269; 148/281; 148/284
(58) Field of Search ................................ 148/269, 281, 148/284, 670, 671, 687

(56) References Cited

U.S. PATENT DOCUMENTS 4,197,643 A    4/1980 Burstone et al.
4,508,578 A  * 4/1985 Wada et al. ................... 148/96
5,169,597 A   12/1992 Davidson et al.
5,477,864 A   12/1995 Davidson
5,690,670 A   11/1997 Davidson
6,258,182 B1   7/2001 Schetky et al.

FOREIGN PATENT DOCUMENTS

| EP | 0 601 804 A1 | 6/1994 | |
| EP | 0 707 085 A1 | 4/1996 | |
| GB | 837636 | 6/1960 | |
| JP | 02061042 A * | 3/1990 | ............. C22F/1/18 |
| JP | 02289266 A * | 11/1990 | .......... A61M/25/01 |
| JP | 4-279212 | 5/1992 | |
| JP | 5-195175 | 8/1993 | |
| JP | 6-63151 | 3/1994 | |
| JP | 6-293929 | 10/1994 | |
| JP | 11-71621 | 3/1999 | |
| JP | 11-276597 | 10/1999 | |
| JP | 2000-297 | 1/2000 | |
| JP | 2000-14792 | 1/2000 | |

OTHER PUBLICATIONS

English Language Translation of JP 02–061042 A, Mar. 1990, Japan, Takahashi et al.*
M.J. Donachie Jr: "Titanium–A Technical Guide" 1998, ASM, Ohio, US XP002155392 p. 58–60.

* cited by examiner

*Primary Examiner*—Andrew L. Oltmans
(74) *Attorney, Agent, or Firm*—Marshall, Gerstein & Borun LLP

(57) ABSTRACT

The diamter of β-titanium alloy wire is reduced by cold wire-drawing and the β-titanium alloy wire is subjected to heat treatment. The heat treatment comprises the first aging process for precipitation strengthening and the second aging process for removing processing strain. β-titanium alloy wire is heat-treated under the supply of tension at the second aging process.

5 Claims, 11 Drawing Sheets

(a)

(b)

(c)

METHOD FOR PRODUCING β-TITANIUM ALLOY WIRE

CROSS-REFERENCE TO RELATED APPLICATION

This is a divisional of U.S. application Ser. No. 09/655,949, filed Sep. 6, 2000 now U.S. Pat. No. 6,402,859.

FIELD OF THE INVENTION

The present invention relates to β-titanium alloy wire which is suitable for metallic wires, such as various kinds of precision springs, various kinds of ropes or cables, tension member for communication cable, probe card pin for inspection of conduction, metallic fishing line and the like. The present invention also relates to a method for producing said β-titanium alloy wire and medical instruments made by said β-titanium alloy wire.

DESCRIPTION OF PRIOR ART

Titanium is hexagonal close-packed structure (hcp, α-structure) at a room temperature. Titanium is converted into body-centered cubic structure (bcc, β-structure) by allotropic transformation at a temperature of 1158 K or more. A density of titanium is about 60% of that of Fe. Titanium's specific strength (proof stress divided by density) is the maximum of all metals. Young's modulus and thermal expansion coefficient of titanium are about a half of stainless steel's value respectively. A specific heat, an electrical conductivity and a thermal conductivity of titanium are much lower than those values of aluminum alloy or magnesium alloy respectively. Titanium has a perfect corrosion-proofness under the oxidation environment. Titanium is corrosion-resistant to chlorine ion. As described above in detail, titanium has many good properties. Accordingly, titanium is widely utilized for heat-conducting pipes of heat exchanger of fossil power station or nuclear power station in which sea water is used for cooling, sea water desalination apparatus, various electrodes for electrolysis, petroleum refining plant and the like.

The equilibrium phase diagrams of two elements containing mainly titanium are classified into α-stabilized type, β-stabilized type, β-eutectoid type, and α–β homogeneous solid solution type. Titanium alloy is obtained by combination of α-stabilized elements which raise α–β transformation point by extending α-phase region to a high temperature part, β-stabilized elements which lower α–β transformation point by extending β-phase region to a lower, temperature part and neutral elements which have no effects on phase-stabilization. For example, there are aluminum and tin as α-stabilized elements, vanadium and chromium as β-stabilized elements, zirconium and hafnium as neutral elements. Titanium alloys are classified into a α-titanium alloy (hcp), α+β type titanium alloy (hcp+bcc), β-titanium alloy (bcc) according to crystal structure of phase constituting micro structure under a normal temperature.

α-titanium alloy is a single phase alloy obtained by solid solution hardening as a result of addition of α-stabilized elements to titanium. Aluminum, which has a large solubility limit to titanium and a high solid solution hardening capacity, is mainly used as the addition element. So, α-titanium alloy is a good oxidation-resistant under a high temperature but a little poor in workability. α+β type titanium alloy is two phase alloy under coexistence of α-phase and β-phase at a normal temperature by addition of α-stabilized elements and β-stabilized elements. Titanium-6aluminum-4vanadium, which is a representative α+β type titanium alloy, has a high specific strength and a high ductility, but shows a brittleness if working conditions would not be enough controlled at hot working.

On the other hand, β-titanium alloy is a single phase alloy obtained by retaining at a normal temperature β-phase which have been formed under a high temperature. β-titanium alloy is good in cold workability and has a high strength and a good ductility due to the heat treatment. Recently a research on β-titanium alloy has been actively conducted. For example, in case of titanium-15 vanadium-3-chromium-3 tin-3 aluminum, when the conditions of cold rolling and solid solution treatment have been optimized, it is reported that a tensile strength of nearly 1900 N/mm$^2$ and an elongation of 10% have been obtained. Patent unexamined publication No. 11-71621 discloses an invention on a method for producing β-phase titanium alloy bar wire which states that it is possible to improve the strength and the ductility by forming working texture of β-phase prior to aging treatment and controlling α-phase transformation texture precipitated by aging treatment. The details of this invention is as follows:

β-phase titanium alloy bar wire is subjected to solution treatment or hot rolling at a temperature of more than transformation temperature, followed by cold working of reduction ratio of area of 30% or more and then annealing at a range between a temperature of 100° C. lower than β-transformation point and a temperature of 10° C. lower than β-transformation point. After that, β-phase titanium alloy bar wire is shaped into a fixed form and subjected to an aging treatment, resulting in obtaining a high strength and a high ductility. This invention is hereinafter referred to as the prior method for producing β-titanium alloy bar wire.

Recently, it has been increasing to perform a diagnosis or a therapy by inserting a catheter into a blood vessel or a digestive tract. As to medical instruments which make use of the catheter, there are a guide wire which is manipulated through the inside of the catheter or a stent which is placed in the aim portion after passing through the inside of catheter.

The explanation of guide wire for medical treatment will be given below. The guide wire for medical treatment is used as a guide for introducing the catheter to perform a minimally invasive treatment. Generally, the guide wire for medical treatment is pushed out from the tip of the catheter and inserted into the blood vessel. For the reason, it is necessary for the guide wire for medical treatment to pass through a serpentine: blood vessel or a stenosis portion (crossability) and selectively go into a requested direction at a junction (selectivity or pushability). Also, it is preferable that the tip of the guide wire for medical treatment would, be a little bent to insert into the catheter and then slightly twisted at the base of wire to select the direction toward which said tip should go by rotating the bent portion of the tip. To give a little bend is referred to as reshaping. Accordingly, the guide wire for medical treatment should have the function that the tip would move correspondingly to the twist motion of the base (torque transmittability).

The guide wire for medical treatment may be roughly divided into two categories. One is such that its center core would be a stainless steel wire and a stainless steel coil would be wound around the distal portion of the stainless steel wire. The other is such that its center core would be a super-elastic alloy and a synthetic resin would cover the center core.

But stainless steel has a high yield strength and a good pushability. Furthermore, stainless steel is easy to make plastic deformation. As a result, when stainless steel is used as center core, it is supposed that the center core would injure the blood vessel wall at its serpentine portion or its stenosis portion. Furthermore, when the plastic deformed guide wire is pulled out, it is feared that the guide wire would injure the blood vessel wall. In addition, it is a large matter that the guide wire made of stainless steel has a very low transmittability of twisting in the serpentine blood vessel and a poor selectivity or operationality at a junction.

On the other hand, the guide wire made of super-elastic alloy has a high torque transmittability in the serpentine blood vessel but it is impossible to make re-shaping at the tip thereof. And the guide wire made of super-elastic alloy has little resistance to bending at a bend portion. For solving the above problems, the guide wire comprising the following features has been demanded. The guide wire should be easily and safely manipulated by a person in attendance on the operation. For the reason, the guide wire needs to have a high elastic modulus, a moderate yield strength and a re-shaping characteristic.

Patent unexamined publication No. 6-63151 discloses the guide wire whose center core comprising Co—Ni—Cr—Fe alloy is coated with plastic resin as new material for center core. However, any alloy disclosed in this publication has an elastic modulus of 20000 kgf/mm$^2$ or more. Such alloy is more unbending than stainless steel and difficult to-make plastic deformation. As a result, it is possible that the alloy would injure the blood vessel wall or extends the serpentine blood vessel when it is inserted into the serpentine blood vessel.

Zirconium-amorphous alloy is disclosed in Patent unexamined publication No. 11-276597 or No. 2000-297. Cu-shape memory alloy is disclosed in Patent unexamined publication No. 2000-14792. These alloys are still under the research stage and have various problems to be solved for the practical material.

Furthermore, U.S. Pat. No. 5,169,597 discloses a transplant piece made of titanium alloy having a low elastic modulus. Expensive niobium and zirconium are essential elements for this transplant piece. In case of utilizing this piece for a center core of guide wire which is machined to a thickness of 0.5 mm or less, the strength of this piece is not enough to be conducted a straight shaping under addition of tension or a tapered shaping at a tip. Accordingly, this transplant piece is not suitable for a continuous tapered shaping, a continuous straight shaping or resin coating. When center core material is manufactured by hot working using this transplant piece, there will appear the following defects. Crystal grain will become coarse and exhibit a low strength. It is difficult to obtain a smooth surface and a roundness due to oxidation of the surface during the hot working. As a result, it is necessary to be worked several times for obtaining the mechanical properties and the shape to meet the needs for the center core of guide wire.

In the catheter, it is needed that the catheter would pass through the serpentine blood vessel or the stenosis portion (pushability or crossability) by providing the catheter with a rigidity by means of introducing the wire into the rumen of the catheter and laying the wire under the catheter wall. Stainless steel wire has been used as the wire for the catheter until now. As a result, the wire for catheter has the same problems as the guide wire for medical treatment.

Stainless steel or nickel-titanium alloy has been used as placement instruments, such as stent, which is placed on the extending portion of the stenosis portion of blood vessel. As to the stent made of stainless steel, there are one which can be obtained by making a stainless steel wire zigzag and another one which can be obtained by providing a stainless steel pipe with various types of openings. However, the prior stent has not satisfied a flexibility for passing through blood vessel and a moderate rigidity after placement to suppress re-stenosis.

The problems to be solved by the present invention are broadly classified into four groups.

(1) First Problem

In accordance with the prior method for producing β-titanium alloy bar wire, β-phase working texture is formed by cold working of reduction ratio of area of 30% or more. Then as a result of annealing at a range between a temperature of 100° C. lower than β-transformation point and a temperature of 10° C. lower than β-transformation point, a randomization of working texture has not arisen with control of recrystallization and the work-hardened bar wire will become soft. Furthermore, since β-phase titanium alloy bar wire is shaped into a fixed form and subjected to an aging treatment, it is possible to precipitate fine α-phase in β-phase and improve the strength.

As described above, in accordance with the prior method for producing β-titanium alloy bar wire, it is possible to heighten the strength and increase the ductility of β-type titanium alloy bar wire. But it is difficult to obtain a straightness (characteristic of being straight). For example, it is impossible to improve the straightness even if the fine β-type titanium alloy wire would be let into a general levelling roller or a rotary leveller. Because β-type titanium alloy wire has a low Young's modulus, even if the mechanical working for straightening the β-titanium alloy wire by plastic deforming using roller would be conducted, an effect of the mechanical working cannot be expected.

It is difficult to apply the prior method for producing β-titanium alloy bar wire to the production of metallic wires which are needed to have the straightness, such as communication cable, probe card pin for inspection of conduction, metallic fishing line and the like.

First problem is to provide the method for producing β-titanium alloy wire with a high strength and a good straightness.

(2) Second Problem

In accordance with the prior method for producing β-titanium alloy bar wire, it is possible to heighten the strength but a low elastic modulus cannot be obtained.

It is difficult to apply the prior method for producing β-titanium alloy bar wire to the production of metallic wires which are needed to have the low Young's modulus (ductility), such as tension member for communication cable, probe card pin for inspection of conduction, metallic fishing line and the like.

Second problem is to provide β-titanium alloy wire and method for its production with a low Young's modulus (ductility) and a high strength.

(3) Third Problem

In accordance with the prior method for producing titanium alloy wire, wire rods have been heated at a temperature of 400 to 650° C. in the atmosphere to generate the oxidation film on the surface of wire rods and a cold wire-drawing has been conducted by making use of lubrication of this film. However, all reduction ratio of area of cold wire-drawing by this prior method is 70% at a maximum. Since the above oxide film is hard and brittle, the oxide film would be cracked owing to a high reduction ratio of area and lubrication action would be lowering. If the cracked boundary face enlarges, titanium alloy wire would be damaged and breaking of wire would be generated. Accordingly, it is necessary to eliminate the embrittled oxide film by pickling and conduct the second treatment for generating the oxide film and repeat cold wire-drawing before enlargement of crack in the oxide film. For the reason, the number of production processes increases and the production cost becomes larger. Especially, in case of β-titanium alloy, α-phase would be precipitated in β-phase and β-titanium would be hardened because of heating at a temperature of 400 to 650° C. in the atmosphere. As a result, long heating extremely lowers cold wire-drawability and brings a deterioration of mechanical strength.

There are the means for downsizing, such as roller die or swaging. But it is impossible to obtain a good circularity and an accuracy of dimension by those means. Accordingly, those would be in need of cold wire-drawing at sequential process.

For solving the above defects, it is disclosed in Patent Unexamined Publication No. 4-279212 that titanium wire is coated with copper and the repetition of cold wire-drawing and annealing are conducted to get thin titanium, wire.

But, in accordance with the above art, since Young's modulus of copper is higher than β-titanium alloy, Young's modulus totally gets higher.

It is difficult to apply this art to the production of metallic wires which are needed to have the high ductility, such as various kinds of precision springs, various kinds of ropes or cables, tension member, metallic fishing line and the like.

Third problem is to provide the method for producing β-titanium alloy wire with a good lubricity and a good wire-drawability and a low wire-drawing cost and a high ductility.

(4) Fourth Problem

In consideration of the above defects on medical treatments, the fourth problem is to provide the guide wire for medical treatment and the catheter with moderate rigidity and ductility. The another problem is to provide the stent having a ductility for passing through the blood vessel and a moderate rigidity after placement to suppress re-stenosis.

SUMMARY OF THE INVENTION

For solving the first problem, the present invention is characterized in that wire-drawing of β-titanium alloy is followed by two stages aging processes. By the first aging process, fine α-phase is precipitated in β-phase to heighten the strength. In the second aging process, since heat treatment is conducted under a supply of moderate tension, strain accompanied by wire-drawing is eliminated to improve the straightness.

For solving the second problem, the present invention is characterized by specifying the shape and the size of the β-phase crystal. By this invention, it is possible to obtain β-titanium alloy wire with a high strength and a low Young's modulus.

For solving the third problem, the present invention is characterized in that center core of β-titanium-alloy is coated with the specified material to get a composite wire. By this invention, it is possible to conduct a cold wire drawing maintaining a good lubricity and a good drawability.

For solving the fourth problem, the present invention is characterized by employing β-titanium alloy wire comprising β-phase crystal grain of the specified shape and size. By this invention, it is possible to provide a guide wire for medical treatment, catheter and stent, each of which has a moderate rigidity and a ductility respectively.

For solving the first, second, third and fourth problems, the present invention has the following features.

(1) The Invention "A" of Method for Producing β-titanium Alloy Wire for Solving the First Problem The gist of the invention "A" is that a method for producing β-titanium alloy wire comprising the steps of reducing the diameter of β-titanium alloy wire by cold wire-drawing followed by heat treatment is characterized in that the heat treatment comprises the first aging process for precipitation strengthening and the second aging process for removing a processing strain, and β-titanium alloy wire is heat-treated under a supply of tension at the second aging process.

In accordance with the present invention, fine α-phase is plentifully precipitated in the β-phase of β-titanium alloy wire to heighten the strength in the first aging process and then β-titanium alloy wire is heat-treated under a supply of moderate tension to remove a strain accompanied by wire-drawing and improve the straightness in the second aging process. In this case, if a solid solution treatment is conducted at a temperature over β-transformation point before cold wire-drawing and the structure is free from α-phase, the cold workability would be improved to facilitate cold wire-drawing and evenly form a deformation texture of β-phase.

β-titanium is good in workability but easy to adhere to the others. It is preferable to coat β-titanium wire with a moderate oxide film before the wire-drawing to avoid the adhesion to the surface of die at the wire-drawing.

Wire-drawing may be conducted by means of cassette roller die or holey die.

The temperature of 425 to 650° C. is desirable for the first aging process. The reason is that if the temperature is over 650° C. over-aging would be improperly done to lower the strength and if the temperature is under 425° C., fine α-phase could not be precipitated in spite of long time aging treatment. The processing time of the first aging process may be fitly set according to the diameter of wire. For example, if the diameter of wire is 10 μm, the time of one minute to several minutes would be satisfactory for the first aging process and if the diameter of wire is 1 mm, the time for the first aging process may be set in the range of 4 to 48 hours. If the processing time is too short, fine α-phase could not be precipitated in plenty. If the processing time is too long, the quantity of precipitated α-phase does not increase so much.

If the temperature of the second aging process is under 300° C., the processing strain could not be removed and the straightness could not be improved even under the supply of tension. If the temperature of the second aging process is over 600° C., the change of metal structure such as solution would be improperly generated to lower the ductility. For this reason, the temperature of 300 to 600° C. is desirable for the second aging process.

If the processing time of the second aging process is too short, the processing strain could not be removed and the straightness could not be improved under the supply of tension. If the processing time is too long, the effect would be not only unchanged but also the production efficiency would be lowered. For this reason, the time of 3 to 10 minutes is desirable for the second aging process.

The strength of 0.1 to 30% of breaking load of β-titanium alloy wire is desirable for the tension to be supplied to β-titanium alloy wire at the second aging process. If the strength is under 0.1% of said breaking load, the degree of improvement fo straightness would be small. If the strength is over 30% of said breaking load, there is a possibility that titanium wire would extend. Furthermore, the strength of 0.5 to 10% of breaking load of β-titanium alloy wire is more desirable for the tension to be supplied to β-titanium alloy wire at the second aging process. There are many machinery structural restrictions and no ecomical merit as actual industrial equipment in case of controlling tension in the range of less than 0.5% of said breaking load. In consideration of the variation in rewinding tension of titanium wire, since it is feared that an instant maximum tension would become much larger than a setting tension, the setting tension of less than 10% of the breaking load is realistic.

Most of the diameter of metallic wires, such as tension member for communication cable, probe card pin for inspection of conduction, metallic fishing line and the like are in the range of 0.01 to 2.0 mm. β-titanium alloy wire of diameter of 0.01 to 2.0 mm is suitable for metallic wire of these applications. Especially, since the required level (as described later) of the straightness of the probe card pin it extremely severe and lower than 0.3 to 50 mm, β-titanium alloy wire of the present invention, which is good in straightness, is suitable for this application.

(2) The Invention "B" of β-titanium Alloy Wire and Method for its Production for Solving the Second Problem The gist of the invention "B" is that β-titanium alloy wire comprises a diameter of 0.01 to 2.0 mm, an average crystal grain area A of β-phase in cross section structure is 1 to 80 $\mu m^2$, an average crystal grain length L of β-phase in vertical section structure is 10 to 1000 $\mu m$ and a ratio of L/√A is 5 to 1000.

The reasons for restricting the factors specifying the shape and the size are as follows:

If the diameter of β-titanium alloy wire is less than 0.01 mm, it is not possible to obtain a practical strength. If the diameter of β-titanium alloy wire is more than 2.0 mm, the wire would have a low Young's modulus but no ductility could not be obtained.

It is very difficult and not realistic to obtain β-titanium alloy wire, whose average crystal grain area A of β-phase in cross section structure is under 1 $\mu m^2$, by wire-drawing. β-titanium alloy, whose average crystal grain area A of β-phase in cross section structure is over 80 $\mu m^2$, shows a low strength and is not desirable for solving the the present invention's problem.

It reveals a defect of being insufficient in strength that an average crystal grain length L of β-phase in vertical section structure is under 10 $\mu m$. It is difficult to obtain β-titanium alloy wire, whose average crystal grain length L of β-phase in vertical section structure is over 1000 $\mu m$, by machining.

As for a relation between an average crystal grain length L and an average crystal grain area A, if L/√A is under 5, it is impossible to obtain a sufficient strength and ductility, and then it is difficult to machine β-titanium alloy wire so that L/√A would be over 1000.

As described above, by restricting a diameter of wire, an average crystal grain area A of β-phase in cross section structure, an average crystal grain length L of β-phase in vertical section structure and a ratio of L/√A to the specified ranges of the present invention, β-titanium alloy wire with a high strength and a low Young's modulus can be obtained.

For producing β-titanium alloy wire of the present invention, It is preferable that β-titanium alloy would be subjected to solid solution treatment at a temperature of more than β-transformation point to get a structure free from α-phase before cold wire-drawing. As a result, cold workability is improved to facilitate cold wire-drawing and evenly form a deformation texture of β-phase.

β-titanium is good in workability but easy to adhere to the others. It is preferable to coat β-titanium alloy wire with a moderate oxide film before wire-drawing to avoid the adhesion to the surface of die at the wire-drawing.

Wire-drawing may be conducted by means of cassette roller die or holey die.

It is possible to precipitate fine α-phase in β-phase and heighten the strength by a moderate aging treatment after wire-drawing. It is preferable that the aging temperature would be in the range of 400 to 600° C. and the aging time would be in the range of 1 to 24 hours.

For obtaining β-titanium alloy wire comprising the above distinctive crystal grain shape, it is necessary that all reduction ratio of area by cold wire-drawing would stand at 70% or more. All reduction ratio of area of 90% or more is desirable for the present invention but all reduction ratio of area of more than 99% would generate a work hardening leading to embrittlement.

Most of the diameter of metallic wires, such as tension member for communication cable, probe card pin for inspection of conduction, metallic fishing line and the like are in the range of 0.01 to 2.0 mm. β-titanium alloy wire of diameter of 0.01 to 2.0 mm to be produced by the method of the present invention is suitable for metallic wire of these applications.

(3) The Invention "C" of Method for Producing β-titanium Alloy Wire for Solving the Third Problem The gist of the invention "C" is characterized in that that a center core of β-titanium alloy is coated with the outer shroud comprising aluminum or aluminum alloy to get a integrated composite wire and then gives the cold wire-drawing to said composite wire.

In accordance with the present invention, since the center core of β-titanium alloy is coated with aluminum or aluminum alloy, β-titanium alloy would not be oxidized and titanium oxide which degrade wire-drawability would not be formed. Since coating of aluminum or aluminum alloy has a good ductility, β-titanium alloy with this coating is little hardened even though cold wire-drawing of high reduction ratio of area would be conducted. Thus, a good wire-drawability and lubricity would be maintained. As a result, it is possible to make cold wire-drawing of all reduction ratio of area of more than 90%. Furthermore, since β-titanium as well as aluminum has a low Young's modulus, young modulus of a integrated compound wire becomes low, too. Therefore, β-titanium alloy wire of good ductility can be obtained.

A stable and sure cold wire-drawing becomes possible through means that a ratio of cross section area of the outer shroud to all cross section area of composite wire before cold wire-drawing is 20 to 60%. If said ratio of cross section area of the outer shroud is under 20%, titanium alloy of center core would be partially exposed at cold wire-drawing, with the result that cold wire-drawability would be lowered. If said ratio of cross section area of the outer shroud is over 60%, the strength per unit cross section area of composite wire would extremely lower, with the result that this composite wire would not be suitable for various kinds of precision springs, various kinds of ropes or cables, tension member, metallic fishing line and the like.

It is more preferable that the above ratio of cross section area of the outer shroud would be 30 to 50%.

For coating the center core of β-titanium alloy with the outer shroud comprising aluminum or aluminum alloy, it is preferable that β-titanium wire passes through aluminum pipe or aluminum alloy pipe and then the center core is adhered closely to the outer shroud by swaging or roller die machining. The composite wire obtained by this manner is repeatedly made cold wire-drawing or heat treatment and the wire comprising the requested size can be obtained.

(4) The Inventions of Guide Wire for Medical Treatment, Catheter and Stent for Solving the Fourth Problem The gist of the invention of guide wire for medical treatment is characterized by employing β-titanium alloy wire that an average crystal grain area A of β-phase in cross section structure is 1 to 80 $\mu m^2$, an average crystal grain length L of β-phase in vertical section structure is 10 to 1000 $\mu m$ and a ratio of L/√A is 5 to 1000.

The gist of the invention of catheter is characterized by employing β-titanium alloy wire that an average crystal grain area A of β-phase in cross section structure is 1 to 80 $\mu m^2$, an average crystal grain length L of β-phase in vertical section structure is 10 to 1000 $\mu m$ and a ratio of L/√A is 5 to 1000.

The gist of the invention of stent is characterized by employing β-titanium alloy wire that an average crystal grain area A of β-phase in cross section structure is 1 to 80 $\mu m^2$, an average crystal grain length L of β-phase in vertical section structure is 10 to 1000 $\mu m$ and a ratio of L/√A is 5 to 1000.

DETAILED DESCRIPTION OF THE PREFERRED EMBODIMENTS

A preferred embodiment will be described below with reference to the figures.

Figure 1:
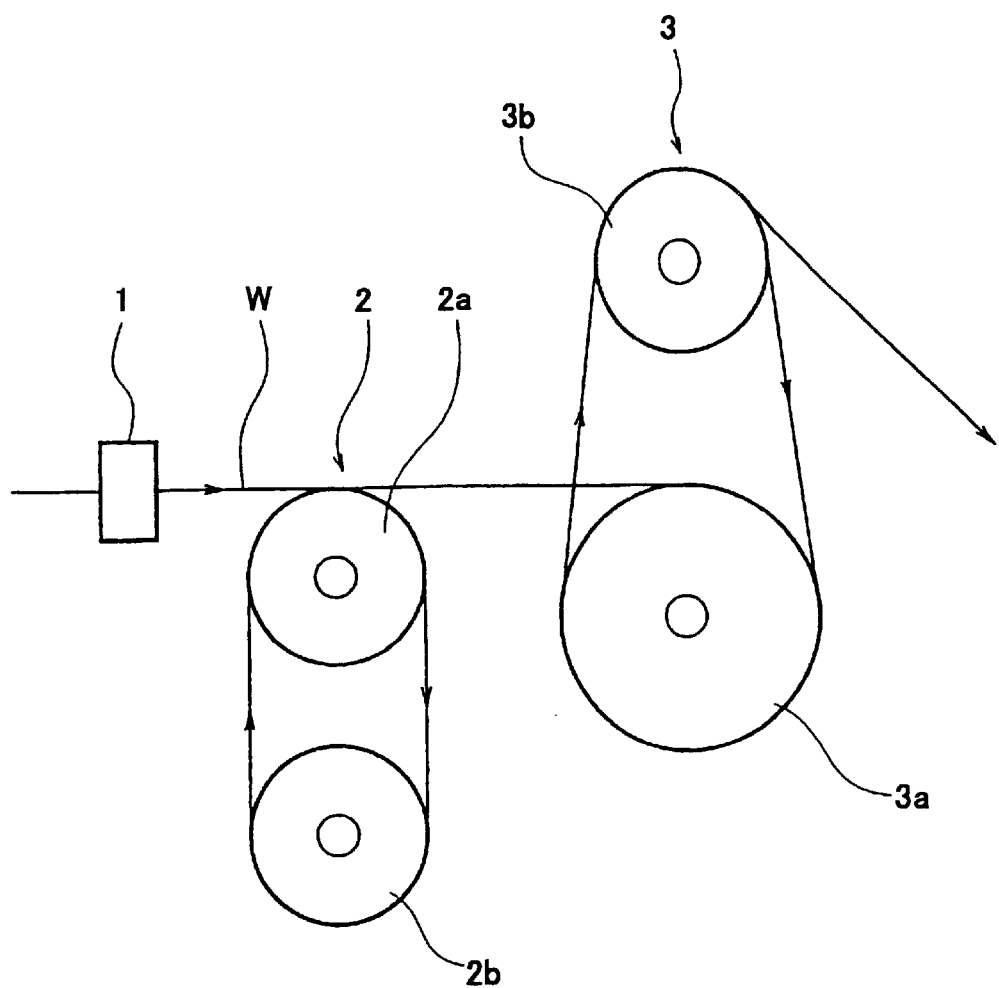
FIG. 1 is a schematic diagram of tension control mechanism installed on the outside of electric furnace in which the second aging process is conducted.

(1) The Method for Producing β-titanium Alloy Wire According to the First Invention A First of all, β-titanium alloy wire of Ti-15V-3Cr-3Sn-3Al comprising the diameter of 3.0 mm was subjected to solid solution treatment under a temperature of 850° C. during 10 minutes (β-transformation point is about 760° C.). And then, this β-titanium alloy wire was heated in oxygen-containing atmosphere at a temperature of 700° C. to form the oxide film. After that, β-titanium alloy wire was wire-drawn to a diameter of 0.3 through 1.0 mm using holey die. Next, this β-titanium alloy wire was inserted into an electric furnace of batch type (not shown) whose heat source was an electric heater to conduct the first aging process in argon gas atmosphere. This β-titanium alloy wire was inserted into an electric furnace of continuous heat-treating type (not shown) whose heat source was an electric heater to conduct the second aging process in argon gas atmosphere. At the same time, as shown in FIG. 1, a tension of β-titanium alloy wire W under the second aging process was controlled by dancer roller 2 in the rear of guide die 1 installed on the outside of electric furnace. And βtitanium alloy wire W was wound onto the winding reel (not shown) through capstan 3.

Dancer roller 2 comprises fixed roller 2a and movable roller 2b. Tension control is conducted by up-and-down motion of movable roller 2b. As movable roller 2b descends, tension will increase. To the contrary, as movable roller 2b ascends, tension will decrease. Tension of β-titanium alloy wire W is measured by load measuring device such as load cell. Actual measurement measured by the load measuring device is converted to an electric signal to give feed-back control. The actual measurement and preset tension value is comparatively calculated. And the modified tension value is converted to an electric signal to transmit to dancer roller 2. Movable roller 2b moves according to the electric signal, with the result that the requested preset tension can be continuously given to β-titanium alloy wire W.

Capstan 3 comprises drive roller 3a and driven roller 3b. β-titanium alloy wire W is taken over to drive roller 3a.

The following table 1 shows diameter of wire, breaking force, temperature and time of the first aging process, temperature and time and tension of the second aging process, and straightness of embodiments and comparative examples. The straightness was measured by means of the method that β-titanium alloy wire was cut into unit lengths to measure the warp. The warp denotes the distance from a straight line connecting both ends of unit length β-titanium alloy wire to middle point of said β-titanium alloy wire. As to the value of this straightness, it is preferable in the field to which β-titanium alloy wire of the present invention is applied that said distance is 0.3 mm or less to the length of the above straight line of 50 mm.

TABLE 1

| | final diameter of wire (mm) | breaking load (kg) | first aging process temp. (° C.) | first aging process time (hr) | second aging process temp. (° C.) | second aging process time (hr) | tension (gr/%)※ | straightness (mm/mm) |
|---|---|---|---|---|---|---|---|---|
| Embodiments | | | | | | | | |
| 1 | 0.5 | 31.0 | 450 | 12 | 450 | 5 | 500/1.6 | 0.08/50 |
| 2 | 0.5 | 32.0 | 425 | 24 | 500 | 3 | 1000/3.1 | 0.05/50 |
| 3 | 1.0 | 119.4 | 500 | 12 | 450 | 5 | 1500/1.3 | 0.05/50 |
| 4 | 1.0 | 117.0 | 550 | 6 | 550 | 3 | 500/0.4 | 0.05/50 |
| 5 | 0.7 | 52.0 | 600 | 2 | 500 | 10 | 100/0.19 | 0.10/50 |
| 6 | 0.3 | 11.0 | 450 | 4 | 300 | 10 | 1000/9.1 | 0.08/50 |
| comparative examples | | | | | | | | |
| 1 | 1.0 | 121.0 | 450 | 12 | 450 | 5 | 50/0.04 | 0.80/50 |
| 2 | 1.0 | 126.4 | 425 | 24 | 500 | 1 | 1000/0.79 | 0.70/50 |
| 3 | 0.5 | 31.0 | 450 | 12 | 200 | 5 | 500/1.6 | 0.55/50 |
| 4 | 0.5 | 30.0 | 500 | 12 | — | — | —/— | 5/50 |

※Tension(%) denotes a ratio of actual force (gr) to breaking force (kg)

As shown in table 1, β-titanium alloy wires of embodiments 1 to 6 are suitable for metallic wires of the field to which β-titanium alloy wire of the present invention is applied because any wire of embodiments 1 to 6 has a low value of straightness.

The value of the straightness of comparative example 1 is high because tension of the second aging process is too low.

The value of the straightness of comparative example 2 is high because time of the second aging process is too short.

The value of the straightness of comparative example 3 is high because temperature of the second aging process is too low.

The value of the straightness of comparative example 4 is extremely high because the second aging process has not been conducted.

(2) β-titanium Alloy Wire and the Method for its Production According to the Second Invention B First of all, β-titanium alloy wire of Ti-15V-3Cr-3Sn-3Al was subjected to solution treatment under a temperature of 850° C. during 10 minutes (β-transformation point is about 760° C.). And then, this β-titanium alloy wire was heated in oxygen-containing atmosphere at a temperature of 700° C. to form the oxide film. After that, β-titanium alloy wire was wire-drawn to a diameter of 0.5 mm using holey die after wire-drawing by roller die. Next, β-titanium alloy wire was subjected to aging process to precipitate fine α-phase in β-phase. The following table 2 shows diameter D of wire just after solution treatment, aging time at a temperature of 450° C., an average crystal grain area A of β-phase in cross section structure, an average crystal grain length L of β-phase in vertical section structure, a ratio of L/√A, all reduction ratio of area at cold wire-drawing, tensile strength and Young's modulus of embodiments and comparative examples. All reduction ratio of area (R.R.A.) is defined below on the condition that $A_0$ is a cross section area of wire just before cold wire-drawing, $A_1$ is a cross section area of wire just after cold wire-drawing.

$$R.R.A.=[(A_0-A_1)/A_0]\times 100 \ (\%)$$

Diameter D of wire just after cold wire-drawing of, β-titanium alloy wire of embodiments and comparative example are unified in 0.5 mm. Aging process condition after cold wire-drawing is in the range of 1 to 24 hours at a temperature of 450° C. Furthermore, table 2 shows tensile strength and Young's modulus of super-elastic Ni—Ti alloy (ref. 1) and stainless steel SUS 304 (ref. 2) for reference.

Figure 2:
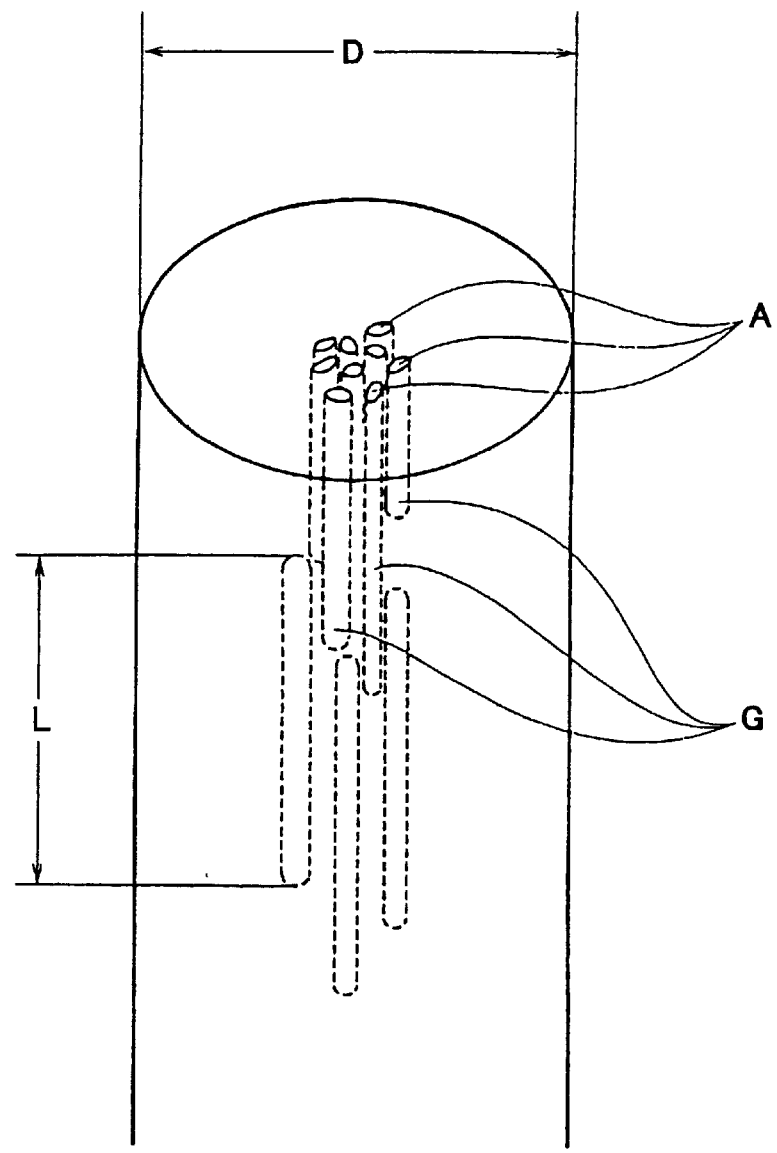
FIG. 2 is an enlarged perspective view showing part of longitudinal direction of β-titanium alloy wire of the present invention.

The signification of terms "A", "L" and diameter D of wire is illustrated in FIG. 2. Term "G" denotes crystal grain.

TABLE 2

| | diameter of wire just after solution treatment D (mm) | aging time (hr) | average crystal grain area of β-phase in vertical section structure A (μm²) | average crystal grain length of β-phase in cross section structure L (μm) | L/√A | all reduction ratio of area (%) | tensile strength (kgf/mm²) | young's modulus (kgf/mm²) |
|---|---|---|---|---|---|---|---|---|
| embodiments | | | | | | | | |
| 1 | 0.96 | 8 | 27.3 | 36.6 | 7.1 | 72.8 | 123.0 | 5670 |
| 2 | 2.94 | 2 | 2.9 | 342.0 | 197.5 | 97.2 | 130.1 | 6230 |
| 3 | 4.39 | 1 | 1.3 | 788.4 | 691.0 | 98.7 | 152.5 | 7520 |
| comparative examples | | | | | | | | |
| 1 | 0.72 | 8 | 48.0 | 20.8 | 3.0 | 51.8 | 95.1 | 5530 |
| 2 | 0.50 | 24 | 225.0 | 16.2 | 1.1 | 0 | 132.7 | 10030 |
| reference 1 | — | — | — | — | — | — | 136.5 | 4367 |
| reference 2 | — | — | — | — | — | — | 220.5 | 13070 |

As shown in table 2, tensile strength and Young's modulus of embodiments 1 to 3 meet the requested levels of tension member for communication cable, probe card pin for inspection of conduction, metallic fishing line and the like. β-titanium alloy wire of the persent invention is suitable for metallic wires of those fields.

But a ratio of L/√A of comparative example 1 is below lower limit of the present invention and its tensile strength is low since all reduction ratio of area at cold wire-drawing is too small.

The purpose of comparative example 2 is to increase a strength due to precipitation of fine α-phase by aging process of 24 hours at a temperature of 450° C. subsequent to making cold wire-drawing at zero of reduction ratio of area. Its average crystal grain area A of β-phase in cross section structure is over upper limit of the present invention, and its ratio of L/√A is below lower limit of the present invention since all reduction ratio of area at cold wire-drawing is zero. Furthermore, its Young's modulus is too large.

Figure 3:
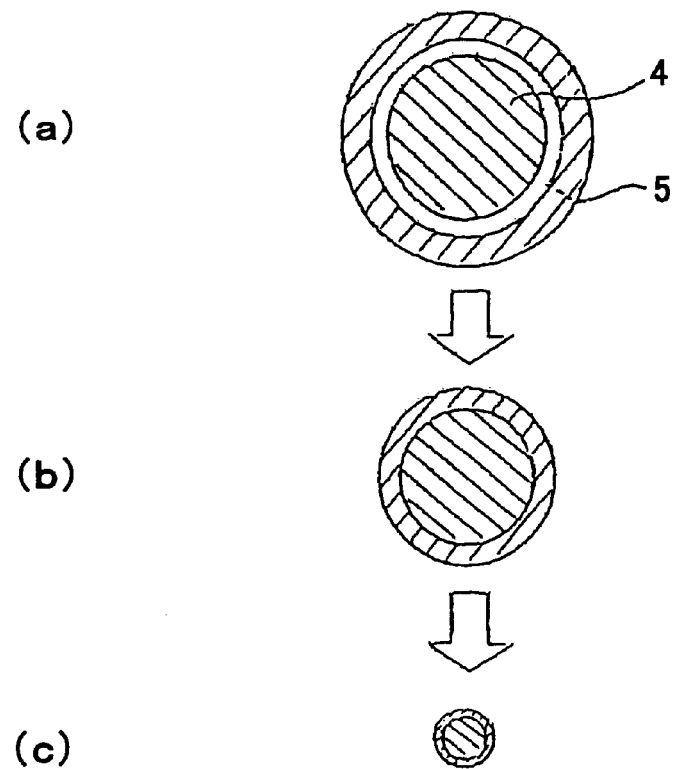
FIG. 3 is a schematic diagram showing manufacturing process of β-titanium alloy wire of the present invention.

(3) The Method for Producing β-titanium Alloy Wire According to the Third Invention C The producing process of β-titanium alloy wire according to the third invention will be explained below with reference to FIG. 3.

Process (a) Center core 4 of β-titanium alloy wire which had been subjected to a solution treatment was passed through outer shroud 5 made of aluminum or aluminum alloy which had a biggish inner diameter than that β-titanium alloy wire.

Process (b) Outer shroud 5 and center core 4 were integrated into one body by swaging and outer shroud 5 was adhered to center core 4.

Process (c) After outer shroud 5 and center core 4 were strongly integrated by roller die processing, cold wire-drawing and heat treatment were repeated to obtain the requested wire.

Figure 4:
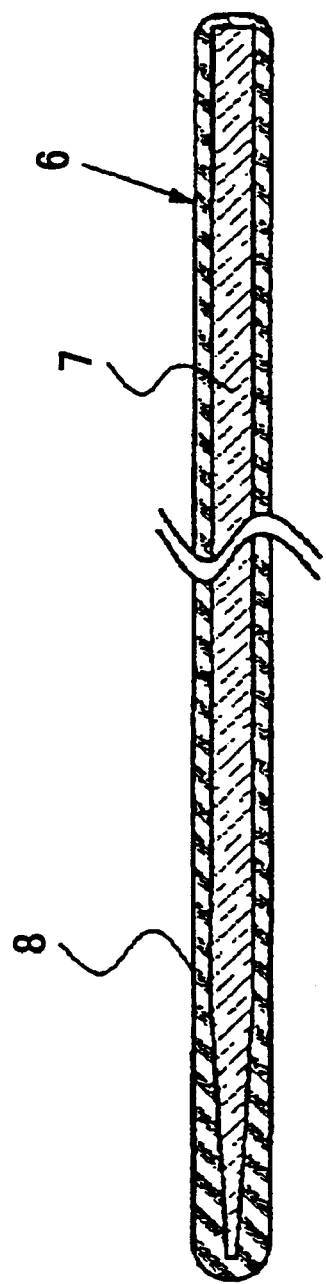
FIG. 4 is a cross section view showing one embodiment of the guide wire for medical treatment of the present invention.

(4) The Guide Wire for Medical Treatment, the Catheter and the Stent of the Present Invention FIG. 4 is a cross section view showing one embodiment of the guide wire for medical treatment of the present invention. Guide wire 6 for medical treatment comprises core member 7 and coating 8 covering all the surface of core member 7. Guide wire 6 for medical treatment has a length of 150 cm but in some cases, a length in the range of 10 to 400 cm is applicable to this case.

An outer diameter of guide wire 6 is 0.89 mm but in some cases, an outer diamter in the range of 0.1 to 2.0 mm is applicable to this case. Outer diameter is nearly the same from the distal portion to the proximal but the distal portion may be thinner than the other portion.

Core member 7 is formed from β-titanium alloy wire as will be mentioned later. Diameter of core member 7 is almost uniform except the distal portion and the distal portion is tapered. Coating 8 is formed from plastic. For example, plastic comprises polyethylene, polyvinyl chloride, polyester, polypropylene, polyamide, polystyrene, polyurethane, fluorocarbon resin and the like. Any of these plastic material sticks to core member 7. Coating 8 may be tube-shaped. It is preferable to make a lubricious coating on the surface of coating 8. In this case, moisture content may be increased by employing hydrophilic surface as a lubricious coating. As a result, it is possible to decrease a friction resistance to blood vessel and improve a sliding characteristic. Furthermore, to make silicon coating, it is possible to improve a sliding characteristic by having a surface comprising a flatness and a low adhesion characteristic to blood.

Various treatments for improving a sliding characteristic may be employed in this case.

β-titanium alloy wire constituting core member 7 has the following properties. Its tensile strength is larger than super-elastic Ni—Ti alloy. Its Young's modulus is about twice that of Ni—Ti alloy and about half of that of stainless steel. Thus, β-titanium alloy wire is excellent in torque transmittability with good toughness and moderate flexibility and recoverability.

β-titanium alloy wire constituting core member 7 has a diameter of 0.49 mm but in some cases, a diameter in the range of 0.1 to 2.0 mm is applicable to this case. As shown in FIG. 2, β-titanium alloy wire is characterized in that an average crystal grain area A of β-phase in cross section structure is 1 to 80 $\mu m^2$, an average crystal grain length L of β-phase in vertical section structure is 10 to 1000 $\mu m$ and a ratio of L/√A is 5 to 1000.

The reasons for restricting the factors specifying the shape and the size are as follows:

It is very difficult and not realistic to obtain β-titanium alloy wire, whose average crystal grain area A of β-phase in cross section structure is under 1 $\mu m^2$, by wire-drawing. β-titanium alloy, whose average crystal grain area A of β-phase in cross section structure is over 80 $\mu m^2$, shows a low strength and is not desirable for solving the the present invention's problem.

It reveals a defect of being insufficient in strength that an average crystal grain length L of β-phase in vertical section structure would be under 10 $\mu m$. It is difficult to obtain β-titanium alloy wire, whose average crystal grain length L of β-phase in vertical section structure is over 1000 $\mu m$, by machining.

As for a relation between an average crystal grain length L and an average crystal grain area A, if L/√A is under 5, it is impossible to obtain a sufficient strength and ductility, and then it is difficult to machine β-titanium alloy wire so that L/√A would be over 1000.

It is preferable that a diameter of β-titanium alloy wire would be 0.01 to 2.0 mm. If the diameter of β-titanium alloy wire is less than 0.01 mm, it is not possible to obtain a practical strength. If the diameter of β-titanium alloy wire is more than 2.0 mm the wire would have a low Young's modulus but no ductility could be obtained.

As described above, by restricting an average crystal grain area A of β-phase in cross section structure, an average crystal grain length L of β-phase in vertical section structure and a ratio of L/√A to the specified ranges of the present invention, β-titanium alloy wire with a moderate rigidity and a ductility and a high strength can be obtained.

For producing β-titanium alloy wire of the persent invention, it is preferable that β-titanium alloy would be subjected to solution treatment at a temperature of more than β-transformation point to get a structure free from α-phase before cold wire-drawing. As a result, cold workability is improved to evenly form a deformation texture of β-phase.

It is preferable that core member 7 of β-titanium alloy wire to be applied to guide wire would have a tensile strength of 110 to 200 $kgf/mm^2$. Its tensile strength of 150 to 180 $kgf/mm^2$ is more preferable. If the tensile strength is lower than 110 $kgf/mm^2$, the strength is not enough to make cold wire-drawing and improve a straightness under a supply of tension. As a result, it is hard to obtain center core having a requested diameter. The straightness of center core will be poor. If the tensile strength is higher than 200 $kgf/mm^2$, Young's modulus becomes higher according to the increase of tensile strength, with the result that the flexibility would go out of existence.

It is preferable that core member 7 of β-titanium alloy wire would have a Young's modulus of 5000 to 10000 kgf/mm². Its Young's modulus of 6000 to 8000 kgf/mm² is more preferable. Young's modulus of lower than 5000 kgf/mm² is not enough for the strength necessary to guide wire. Consequently, a force of inserting the guide wire by hand can be hardly transmitted to the distal portion through the body of the guide wire. If Young's modulus of the guide wire is larger than 10000 kgf/mm², the torsional force cannot be transmitted through the guide wire in the serpentine blood vessel because the guide wire is stiff.

It is preferable that core member 7 of β-titanium alloy wire would have a circularlity of geometrical distorsion of less than 15 μm. The geometrical distorsion of less than 5 μm is more preferable. The geometrical distorsion of less than 1 μm is most preferable. If a circularlity of geometrical distorsion is more than 15 μm, the small variation in torsional force of rotating the guide wire by hand cannot be correctly transmitted to the distal portion through the body of the guide wire in the curved blood vessel and the selectivity at a junction of blood vessel will be poor.

It is preferable that core member 7 of β-titanium alloy wire would have a modulus of rigidity of 1500 to 6000 kgf/mm². Its modulus of rigidity of 3000 to 5000 kgf/mm² is more preferable. If the modulus of rigidity is less than 1500 kgf/mm², the torsional torque of rotating the guide wire by hand cannot be instantly transmitted to the distal portion. If the modulus of rigidity is larger than 6000 kgf/mm², the small variation in the torsional torque of rotating the guide wire by hand cannot be correctly transmitted to the distal portion through the body of the guide wire.

It is preferable that core member 7 of β-titanium alloy wire would have a proof stress of 50 to 150 kgf/mm². Its proof stress of 100 to 130 kgf/mm² is more preferable. If the proof stress is less than 50 kgf/mm², the guide wire would be easily plastic-deformed. If the proof stress is larger than 150 kgf/mm², it is difficult for a person in attendance on the operation to make a re-shaping and it is impossible to give the selectivity to the tip.

It is preferable that core member 7 of β-titanium alloy wire would have a modulus of bending elasticity of 6000 to 18000 kgf/mm². Its modulus of bending elasticity of 10000 to 15000 kgf/mm² is more preferable. The modulus of bending elasticity of lower than 6000 kgf/mm² is not enough for the strength necessary to guide wire. Consequently, a force of rotating the guide wire by hand can be hardly transmitted to the distal portion through the body of the guide wire. If the modulus of bending elasticity is larger than 18000 kgf/mm², the guide wire would unbend the serpentine blood vessel by force, with the result that the blood vessel would be injured.

It is most preferable that core member 7 is provided with all of the above properties. Core member 7 should have one property at least.

It is preferable that center core 7 is provided with two or more of the above properties. For example, β-titanium alloy wire, which has a tensile strength of 110 to 200 kgf/mm² or Young's modulus of 5000 to 10000 kgf/mm² and a circularlity of prescribed geometrical distorsion, is applicable for guide wire. β-titanium alloy wire, which has a tensile strength or Young's modulus of the above range of values and a modulus of rigidity of the above range of values, is applicable for guide wire. β-titanium alloy wire, which has a circularlity of prescribed geometrical distorsion and a modulus of rigidity of the above range of values, is applicable for guide wire.

Titanium alloy wire constituting core member 7 includes titanium (Ti)), molybdenum (Mo), vanadium (V), tungsten (W), niobium (Nb), tantalum (Ta), iron (Fe), chromium (Cr), nickel (Ni), cobalt (Co), aluminum (Al), zirconium (Zr), tin (Sn) and the like.

Figure 5:
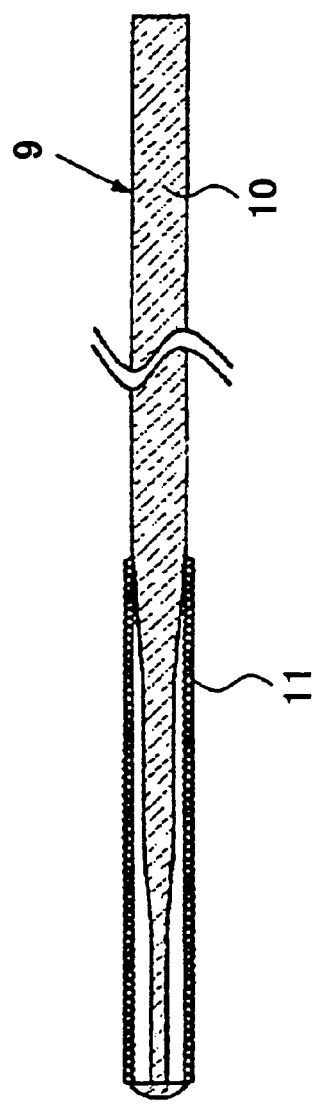
FIG. 5 is a cross section view showing another embodiment of the guide wire for medical treatment of the present invention.

FIG. 5 is a cross section view showing another embodiment of the guide wire for medical treatment of the present invention. Guide wire 9 for medical treatment comprises core member 10 and covering portion 11 covering the surface of the distal portion of the core member 10. Guide wire 9 for medical treatment has a length of 180 cm but in some cases, a length in the range of 10 to 400 cm is applicable to this case. An outer diameter of guide wire 9 is 0.36 mm (0.014 inch) but in some cases, an outer diamter in the range of 0.2 to 2.0 mm is applicable to this case.

Core member 10 is formed from β-titanium alloy. β-titanium alloy wire constituting core member 10 has a diameter of 0.36 mm but in some cases, a diameter in the range of 0.1 to 2.0 mm is applicable to this case. As described above, β-titanium alloy wire is characterized in that an average crystal grain area A of β-phase in cross section structure is 1 to 80 μm², an average crystal grain length L of β-phase in vertical section structure is 10 to 1000 μm and a ratio of $L/\sqrt{A}$ is 5 to 1000.

Covering portion 11 is formed from coil-shaped material. Covering portion may be formed from coating of plastic. Covering portion 11 formed from coil-shaped material is made of stainless steel and its length is in the range of 1 to 50 cm. It is preferable that the distal of the coil-shaped material constituting covering portion 11 would have more radiopaque than that of the other portion. For example, gold, platinum, iridium or alloy of those metals are applicable for the distal of the coil-shaped material constituting covering portion 11. The above materials on guide wire 6 would be applicable for coating of plastic. Covering portion 11 may be tube-shaped. It is preferable to make a lubricious coating on the surface of covering portion 11. In this case, moisture content may be increased by employing hydrophilic surface as a lubricious coating. As a result, it is possible to decrease a friction resistance to blood vessel and improve a sliding characteristic. Furthermore, by cilicon coating, it is possible to improve a sliding characteristic by having a surface comprising a flatness and a low adhesion characteristic to blood. Various treatments for improving a sliding characteristic may be employed.

β-titanium alloy wire constituting center core 10 has the following properties. Its tensile strength is larger than that of super-elastic Ni—Ti alloy. Its Young's modulus is about twice that of Ni—Ti alloy and about half of that of stainless steel. β-titanium alloy wire is excellent in torque transmittability with good toughness and moderate flexibility and recoverability.

As shown in FIG. 5, core member 10 may be formed by the same material from the distal to the proximal. In this case, the outer diameter should be varied according to the requested characteristic of the part. For example, it is preferable that the part except the tip would have a relatively high rigidity to easily transmit a force of inserting the guide wire by hand to the distal. And for transmitting the torque to the distal with easiness, it is preferable that the part except the distal would have a larger diameter than the distal and a taper portion comprising two or more sections that taper toward a very flexible distal. In this case, a wire made of the other material different from titanium alloy may be employed according to the requested characteristic of the part. In the guide wire for medical treatment in which the core member of the distal is made of Ni—Ti alloy and the core member of the proximal is made of titanium alloy, the proximal would have a good pushability and a good torque transmittability and at the same time the tip would have a good blood vessel followability and a good blood vessel crossability due to a good restoring force of Ni—Ti alloy. In the guide wire for medical treatment in which the core member of the distal is made of titanium alloy and the core member of the proximal s made of stainless steel, the proximal would have a good pushability and at the same time the distal would be difficult to kink and make a plastic deformation and the distal would have a good torque transmittability.

It is preferable that β-titanium alloy constituting core member 10 would have a tensile strength of 110 to 200 kgf/mm². Its tensile strength of 150 to 180 kgf/mm² is more preferable. If the tensile strength is lower than 110 kgf/mm², the strength is not enough to make cold wire-drawing and improve a straightness under a supply of tension. As a result, it is hard to obtain the core member having a requested diameter. The straightness of center core will be poor. If the tensile strength is higher than 200 kgf/mm², Young's modulus becomes higher according to the increase of tensile strength, with the result that the flexibility would go out of existence.

It is preferable that core member 10 of β-titanium alloy wire would have a Young's modulus of 5000 to 10000 kgf/mm². Its Young's modulus of 6000 to 8000 kgf/mm² is more preferable. Young's modulus of lower than 5000 kgf/mm² is not enough for the strength necessary to guide wire. Consequently, a force of inserting the guide wire by hand can be hardly transmitted to the distal portion through the body of the guide wire. If Young's modulus of the guide wire is larger than 10000 kgf/mm², the torsional force would be inadequately transmitted through the guide wire in the serpentine blood vessel because the guide wire is stiff.

It is preferable that β-titanium alloy wire constituting core member 10 would have a circularlity of geometrical distorsion of less than 15 μm. The geometrical distorsion of less than 5 μm is more preferable. The geometrical distorsion of less than 1 μm is most preferable. If a circularlity of geometrical distorsion is more than 15 μm, the torque would be inadequately transmitted to the distal portion through the body of the guide wire in the curved blood vessel.

It is preferable that β-titanium alloy wire constituting core member 10 would have a modulus of rigidity of 1500 to 6000 kgf/mm². Its modulus of rigidity of 3000 to 5000 kgf/mm² is more preferable. If the modulus of rigidity is less than 1500 kgf/mm², the torsional torque of rotating the guide wire by hand cannot be instantly transmitted to the distal. If the modulus of rigidity is larger than 6000 kgf/mm², the small variation in torsional torque of rotating the guide wire by hand cannot be correctly transmitted to the distal through the guide wire.

It is preferable that β-titanium alloy wire constituting core member 10 would have a proof stress of 50 to 150 kgf/mm². Its proof stress of 100 to 130 kgf/mm² is more preferable. If the proof stress is less than 50 kgf/mm², the guide wire would be easily plastic-deformed. If the proof stress is larger than 150 kgf/mm², it is difficult for a person in attendance on the operation to make a re-shaping and it is impossible to give the selectivity to the distal.

It is preferable that β-titanium alloy wire constituting core member 10 would have a modulus of bending elasticity of 6000 to 18000 kgf/mm². Its modulus of bending elasticity of 10000 to 15000 kgf/mm² is more preferable. The modulus of bending elasticity of lower than 6000 kgf/mm² is not enough for the strength necessary to guide wire. Consequently, a force of inserting the guide wire by hand can be hardly transmitted to the distal through the guide wire. If the modulus of bending elasticity is larger than 18000 kgf/mm², the guide wire would unbend the serpentine blood vessel by force, with the result that the blood vessel would be injured.

It is most preferable that core member 10 is provided with all of the above properties. Core member 10 should comprise one property at least.

It is preferable that core member 10 is provided with two or more of the above properties. For example, β-titanium alloy wire, which has a tensile strength of 110 to 200 kgf/mm² or Young's modulus of 5000 to 10000 kgf/mm² and a circularlity of prescribed geometrical distorsion, is applicable for guide wire. β-titanium alloy wire, which has a tensile strength or Young's modulus of the above range of values and a modulus of rigidity of the above range of values, is applicable for guide wire. β-titanium alloy wire, which has a circularlity of prescribed geometrical distorsion and a modulus of rigidity of the above range of values, is applicable for guide wire.

Titanium alloy wire constituting core member 10 includes titanium (Ti)), molybdenum (Mo), vanadium (V), tungsten (W), niobium (Nb), tantalum (Ta), iron (Fe), chromium (Cr), nickel (Ni), cobalt (Co), aluminum (Al), zirconium (Zr), tin (Sn) and the like.

β-titanium alloy constituting core member 10 can be produced as described above in case of center core 7.

If the core member of guide wire is made of β-titanium alloy wire, the guide wire would have a characteristic of difficulty in kinking and being deformed and a good torque transmittability. As a result, it is possible to surely and smoothly insert the guide wire into the inside of blood vessel and engage the catheter onto the outside of guide wire. That is, the guide wire can be provided with a high operationality that the tip would make a good response to a torsional force of rotating the guide wire by hand maintaining a high strength and a high elasticity. Furthermore, the tip can be shaped by re-shaping when the occasion demands and since the center core has a moderate rigidity, a good pushability at a stenosis portion and a good selectivity at a junction can be obtained.

Figure 6:
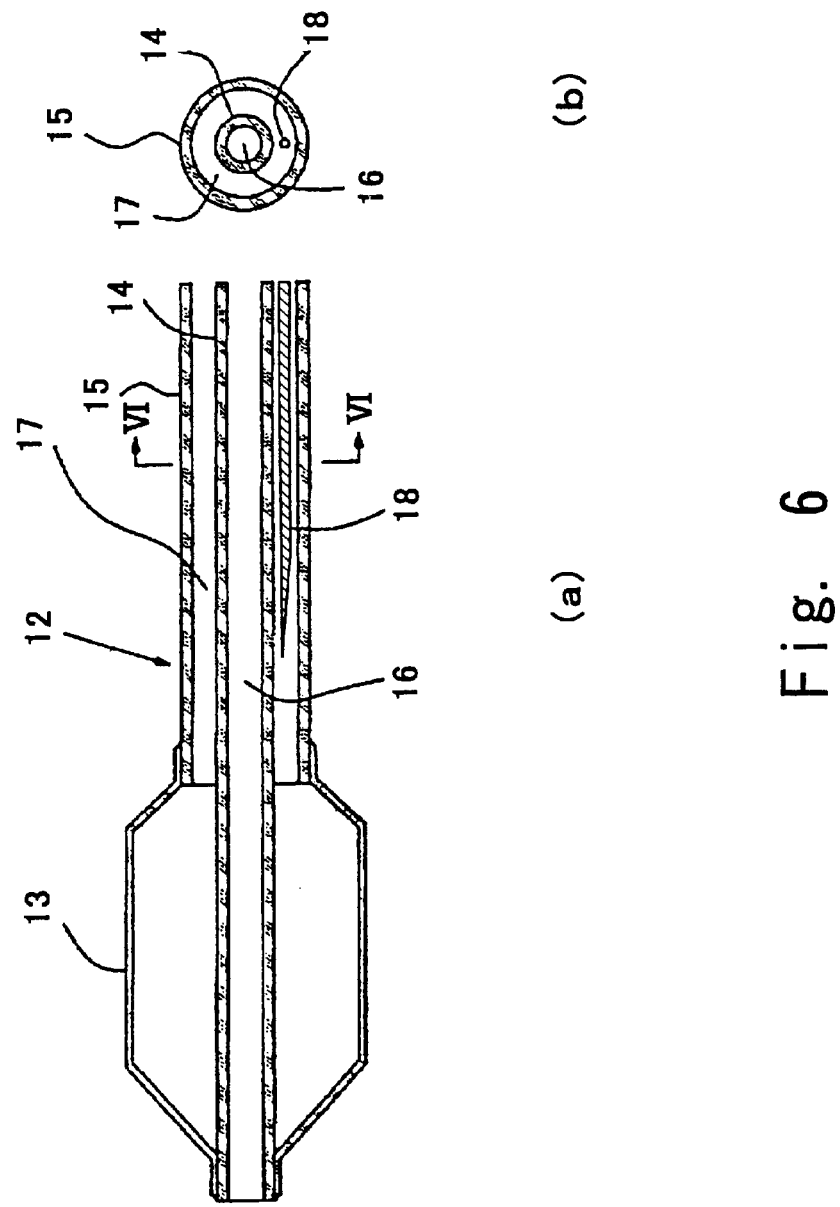
FIG. 6(a) is a cross section view of the distal portion showing one embodiment of the catheter of the present invention and FIG. 6(b) is a cross section view indicated by arrows VI—VI in FIG. 6(a).

FIG. 6(a) is a cross section view of the distal portion showing one embodiment of the catheter of the present invention and FIG. 6(b) is a cross section view indicated by arrows VI—VI in FIG. 6(a). Catheter 12 has a balloon 13 at the distal portion. The distal of balloon 13 is connected to inner tube 14 and the base of balloon 13 is connected to outer tube 15. The inside of inner tube 14 is rumen 16 into which guide wire would be inserted. The space between inner tube 14 and outer tube 15 is rumen 17 for streaming a liquid to extend balloon 13.

Core member 18 is installed from the base (not shown) of catheter 12 to the vicinity of the base of balloon 13 in rumen 17. The distal of core member 18 tapers so that the flexibility of catheter 12 would change gradually. The base of center core 18 is fixed to the base of catheter 12 but might be movable so that a hardness of catheter 12 would be altered freely. Core member 18 might be embedded in inner tube 14 and/or outer tube 15.

β-titanium alloy wire constituting core member 18 is characterized in that an average crystal grain area A of β-phase in cross section structure is 1 to 80 μm², an average crystal grain length L of β-phase in vertical section structure is 10 to 1000 μm and a ratio of L/√A is 5 to 1000.

The reasons for restricting the factors specifying the shape and the size are as follows:

It is very difficult and not realistic to obtain β-titanium alloy wire, whose average crystal grain area A of β-phase in cross section structure is under 1 μm², by wire-drawing. β-titanium alloy, whose average crystal grain area A of β-phase in cross section structure is over 80 μm² shows a low strength and is not desirable for solving the present invention's problem.

It reveals a defect of being insufficient in strength that an average crystal grain length L of β-phase in vertical section structure would be under 10 μm. It is difficult to obtain β-titanium alloy wire, whose average crystal grain length L of β-phase in vertical section structure is over 1000 ì m, by machining.

As for a relation between an average crystal grain length L and an average crystal grain area A, if L/√A is under 5, it is impossible to obtain a sufficient strength and ductility, and then it is difficult to machine β-titanium alloy wire so that L/√A would be over 1000.

It is preferable that a diameter of β-titanium alloy wire would be 0.01 to 2.0 mm. If the diameter of β-titanium alloy wire is less than 0.01 mm, it is not possible to obtain a practical strength. If the diameter of β-titanium alloy wire is more than 2.0 mm, the wire would have a low Young's modulus but no ductility could be obtained.

By restricting the factors to the above extent, β-titanium alloy wire, which has a moderate rigidity and a flexibility and a high strength, can be obtained. Catheter 12 with core member 18 made of said wire is firm and easy to be pushed and inserted into the serpentine blood vessel.

Catheter 12 would be used as described below. A guide wire is from the base of catheter 12 with shrinked and folded balloon 13 to rumen 16 of inner tube 14. The guide wire projects from the distal of balloon 13 and goes on inside the blood vessel to arrive at a destination point comprising a stenosis portion in the inside of blood vessel. After the guide wire has been placed in the destination point, catheter 12 is guided to the above destination point along the guide wire. Generally, since inner tube 14 and outer tube 15 of catheter 12 are made of flexible plastic, a force of inserting the guide wire by hand can be hardly transmitted to the distal. But, since catheter 12 of the present invention has core member 18 made of β-titanium alloy wire comprising a moderate rigidity and a flexibility, a force of inserting the guide wire by hand can be easily transmitted to the tip and catheter 12 of the present invention can follow the serpentine blood vessel. After catheter has been inserted to the destination point, liquid (contrast medium) is injected from the base of catheter 12 to rumen 17 to dilate the stenosis portion. By filling of the liquid, folded balloon 13 would be expanded and the stenosis portion would be dilated.

Figure 7:
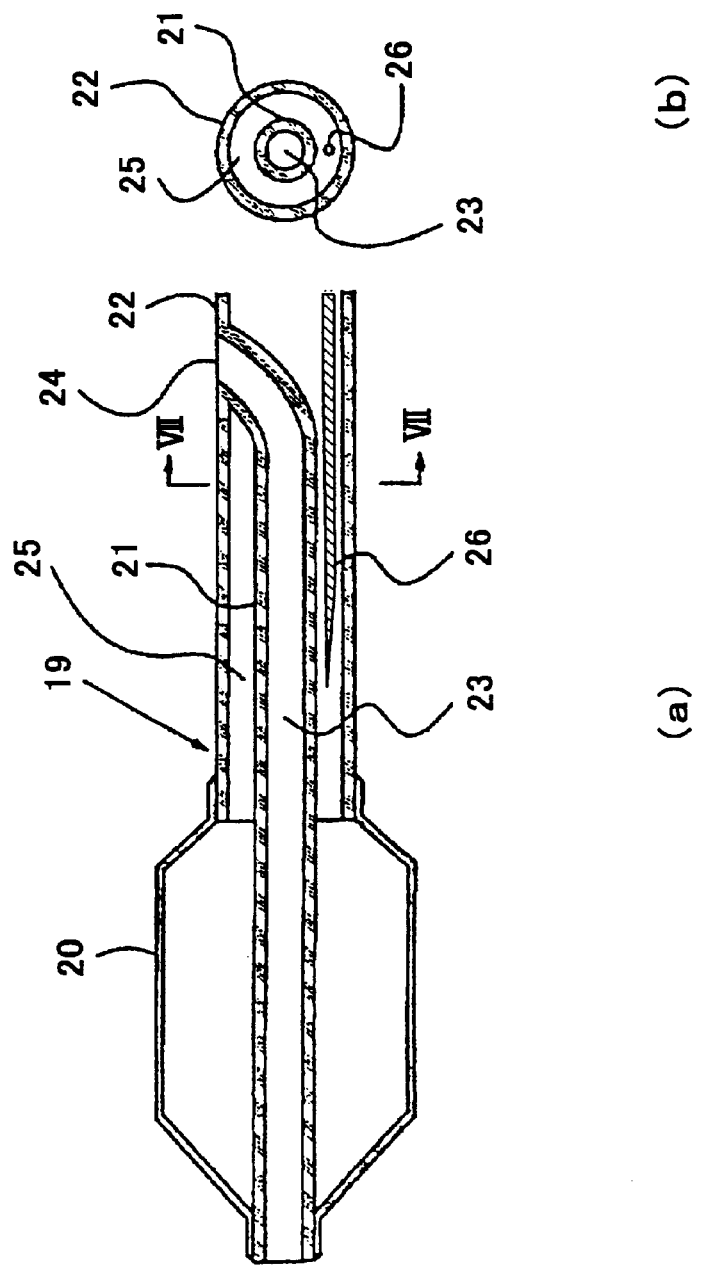
FIG. 7(a) is a cross section view of the distal portion showing another embodiment of the catheter of the present invention and FIG. 7(b) is a cross section view indicated by arrows VII—VII in FIG. 7(a).

FIG. 7(a) is a cross section view of the distal potion showing another embodiment of the catheter of the present invention and FIG. 7(b) is a cross section view indicated by arrows VII—VII in FIG. 7(a).

Catheter 19 has a balloon 20 at the distal. The distal of balloon 20 is connected to inner tube 21 and the base of balloon 20 is connected to outer tube 22. The inside of inner tube 21 is rumen 23 into which guide wire would be inserted. Rumen 23 is communicated to opening 24 installed at a certain distance from the distal. The space between inner tube 21 and outer tube 22 is rumen 25 for streaming a liquid to expanded balloon 20.

Core member 26 is installed from the base (not shown) of catheter 19 to the vicinity of the base of balloon 20 through opening 24 in rumen 25. The distal of core member 26 tapers so that the flexibility of catheter 19 would change gradually. The base of core member 26 is fixed to the base of catheter 19 but might be movable so that a hardness of catheter 19 would be altered freely. Core member 26 might be embedded in inner tube 21 and/or outer tube 22.

β-titanium alloy wire constituting core member 26 is characterized in that an average crystal grain area A of β-phase in cross section structure is 1 to 80 μm², an average crystal grain length L of β-phase in vertical section structure is 10 to 1000 μm and a ratio of L/√A is 5 to 1000.

By restricting the factors to the above extent, β-titanium alloy wire, which has a moderate rigidity and a flexibility and a high strength, can be obtained. Catheter 19 with core member 26 made of said wire is firm and easy to be pushed and inserted into the serpentine blood vessel.

Catheter 19 would be used as described above in case of catheter 12 except that guide wire is inserted in a different way. A guide wire is from the opening 24 of catheter 19 with shrinked and folded balloon 20 to inner tube 21. The guide wire projects from the distal of balloon 20 and goes on inside the blood vessel to arrive at a destination point comprising a stenosis portion in the inside of blood vessel. After the guide wire has been placed in the destination point, catheter 19 is guided to the above destination point along the guide wire. Generally, since inner tube 21 and outer tube 22 of catheter 19 are made of flexible plastic, a force of inserting the guide wire by hand can be hardly transmitted to the tip. But, since catheter 19 of the present invention has core member 26 made of β-titanium alloy wire comprising a moderate rigidity and a flexibility, a force of inserting the guide wire by hand can be easily transmitted to the tip by reinforcing the vicinity of opening 24 and catheter 19 of the present invention can follow the serpentine blood vessel. After catheter has been inserted to the destination point, liquid (contrast medium) is injected from the base of catheter 19 to rumen 25 of inner tube 21 and outer tube 22 to dilate the stenosis portion. By filling of the liquid, folded balloon 20 would be expanded and the stenosis portion would be dilated. If the diameter of expanded balloon does not fit the diameter of blood vessel, catheter 19 should be exchanged. In this case, keeping the guide wire placing in the destination point, it is preferable to pull the inserted catheter 19 out of blood vessel and insert a guide wire into rumen 23 of another catheter 19.

Figure 8:
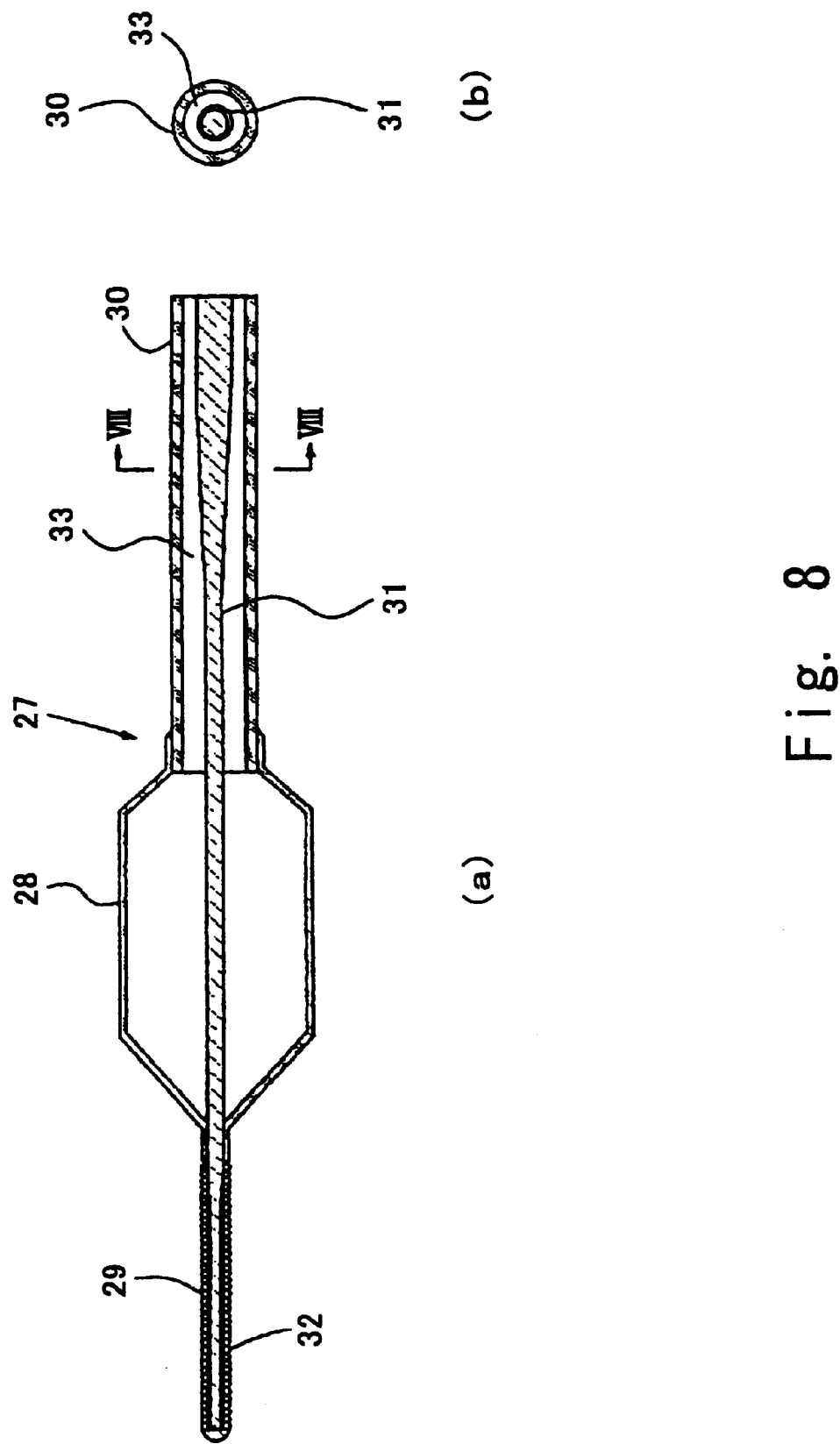
FIG. 8(a) is a cross section view of the distal portion showing further another embodiment of the catheter of the present invention and FIG. 8(b) is a cross section view indicated by arrows VIII—VIII in FIG. 8(a).

FIG. 8(a) is a cross section view of the distal portion showing another embodiment of the catheter of the present invention and FIG. 8(b) is a cross section view indicated by arrows VIII—VIII in FIG. 8(a).

Catheter 27 has a balloon 28 at the distal. The distal of balloon 28 is connected to guide member 29 and the base of balloon 28 is connected to tubular member 30.

Core member 31 is installed in the inside space of tubular member 30 and balloon 28. Core member 31 is connected to the distal of balloon 28 and extends in coil 32 and is fixed to coil 32 at the distal portion thereof. Guide member 29 comprises core member 31 and coil 32 covering the core member. In tubular member 30, core member 31 has a thin part toward the distal through a taper portion. In guide member 29, core member 31 has a thinner part at the distal through a taper portion. The base of core member 31 is fixed to the base of catheter 27. The space between core member 31 and tubular member 30 is rumen 33 for injecting a liquid to extend balloon 28.

β-titanium alloy wire constituting core member 31 is characterized in that an average crystal grain area A of â-phase in cross section structure is 1 to 80 μm², an average crystal grain length L of β-phase in vertical section structure is 10 to 1000 μm and a ratio of L/√A is 5 to 1000.

By restricting the factors to the above extent, β-titanium alloy wire, which has a moderate rigidity and a flexibility and a high strength, can be obtained. Catheter 27 with center core 31 made of said wire is firm and easy to be pushed and besides has a flexibility to follow the serpentine blood vessel. In the above example, β-titanium alloy wire has been employed over the entire length of core member 31. A flexible material such as Ni—Ti alloy wire might be connected to the tip of core member 31 by another connecting means. A rigid material such as stainless steel wire might be connected to the base of core member 31 by another connecting means.

Catheter 27 may be inserted into blood vessel by use of guide member 29 such as guide wire.

Catheter 27 with shrinked and folded balloon 28 goes on the inside of blood vessel to a destination point comprising a stenosis portion. Since catheter 27 of the present invention has core member 31 made of β-titanium alloy wire comprising a moderate rigidity and a flexibility, a force of inserting the guide wire by hand can be easily transmitted to the tip and catheter 27 of the present invention can follow the serpentine blood vessel. After catheter has been inserted to the destination point, liquid (contrast medium) is injected from the base of catheter 27 to rumen 33 to dilate the stenosis portion. By filling of the liquid, folded balloon 28 would be expanded and the stenosis portion would be dilated.

Figure 9:
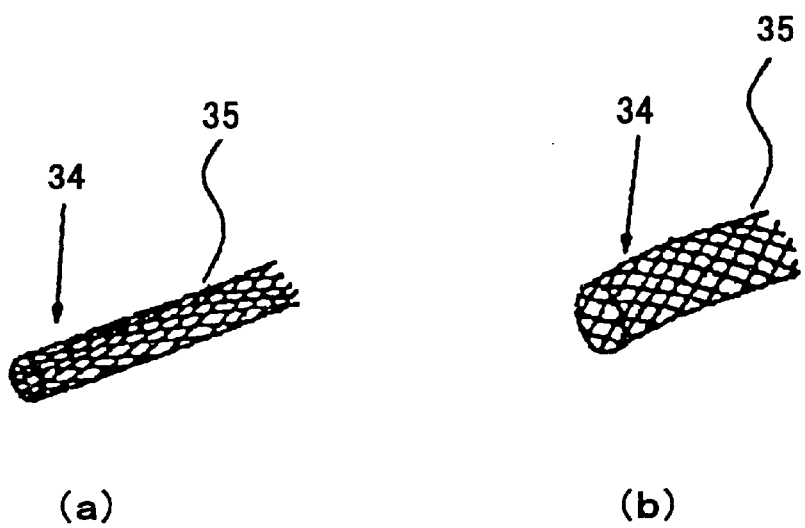
FIG. 9(a) is a perspective view showing a shrinked state of the stent of the present invention and FIG. 9(b) is a perspective view showing an extended state of the stent of the present invention.

FIG. 9(*a*) is a perspective view showing a shrinked state of the stent of the present invention and FIG. 9(*b*) is a perspective view showing an extended state of the stent of the present invention. Stent 34 is a tubular member comprising mesh β-titanium alloy wire 35. Stent 34 is shrinked as shown in FIG. 9(*a*). Stent 34 is extended by balloon as shown in FIG. 9(*b*). By the extension, stent has a high resistance to the external pressure to prevent the stenosis portion from being occluded.

Figure 10:
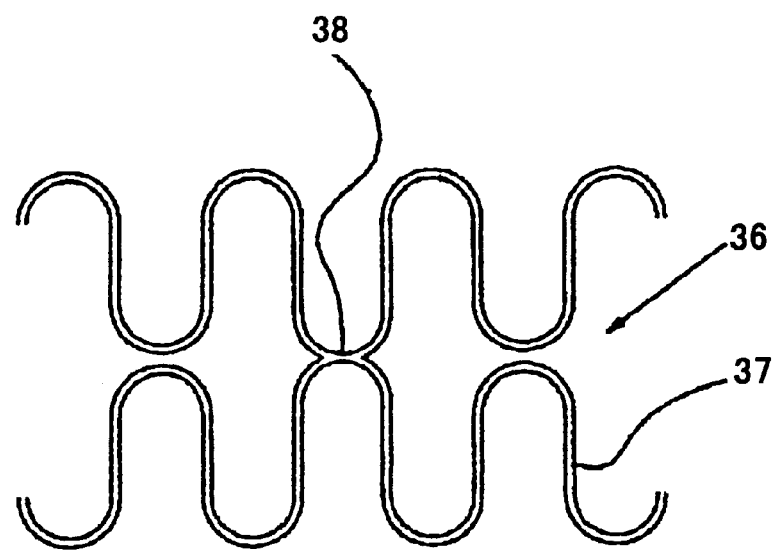
FIG. 10 is a partly enlarged view showing another embodiment of the stent of the present invention.

Stent 36 of FIG. 10 has a construction that β-titanium alloy wire 37 is curved and two tops 38 are fixed together.

β-titanium alloy wire constituting stents 34 and 36 is characterized in that an average crystal grain area A of β-phase in cross section structure is 1 to 80 $\mu m^2$, an average crystal grain length L of β-phase in vertical section structure is 10 to 1000 $\mu m$ and a ratio of L/$\sqrt{A}$ is 5 to 1000.

The reasons for restricting the factors specifying the shape and the size are as follows:

It is very difficult and not realistic to obtain β-titanium alloy wire, whose average crystal grain area A of β-phase in cross section structure is under 1 $\mu m^2$, by wire-drawing. β-titanium alloy, whose average crystal grain area A of β-phase in cross section structure is over 80 $\mu m^2$, shows a low strength and is not desirable for solving the present invention's problem.

It reveals a defect of being insufficient in strength that an average crystal grain length L of β-phase in vertical section structure is under 10 $\mu m$. It is difficult to obtain β-titanium alloy wire, whose average crystal grain length L of μ-phase in vertical section structure is over 1000 $\mu m$, by machining.

As for a relation between an average crystal grain length L and an average crystal grain area A, if L/$\sqrt{A}$ is under 5, it is impossible to obtain a sufficient strength and a ductility, and then it is difficult to machine β-titanium alloy wire so that L/$\sqrt{A}$ would be over 1000.

It is preferable that a diameter of β-titanium alloy wire would be 0.01 to 2.0 mm. If the diameter of β-titanium alloy wire is less than 0.01 mm, it is not possible to obtain a practical strength. If the diameter of β-titanium alloy wire is more than 2.0 mm, the wire would have a low Young's modulus but no flexibility could be obtained.

By restricting the factors to the above extent, β-titanium alloy wire, which has a moderate rigidity and a flexibility and a high strength, can be obtained. Stent made of said β-titanium alloy wire has a flexibility to pass through blood vessel and a moderate rigidity to prevent the extended portion from being occluded. That is, if the stent is stiff, it is difficult for the stent to pass through the bent blood vessel. But, since the stent of the present invention is formed from a flexible titanium alloy wire, it is easy for the stent to pass through the bent blood vessel. After the stent has been extended and placed at the spot, the acute occlusion can be prevented because of the high resistance to the external pressure. Furthermore, since the stent of the present invention is more flexible than stainless steel and has a moderate resistance to the external pressure, it is low stimulant to a living body.

Figure 11:
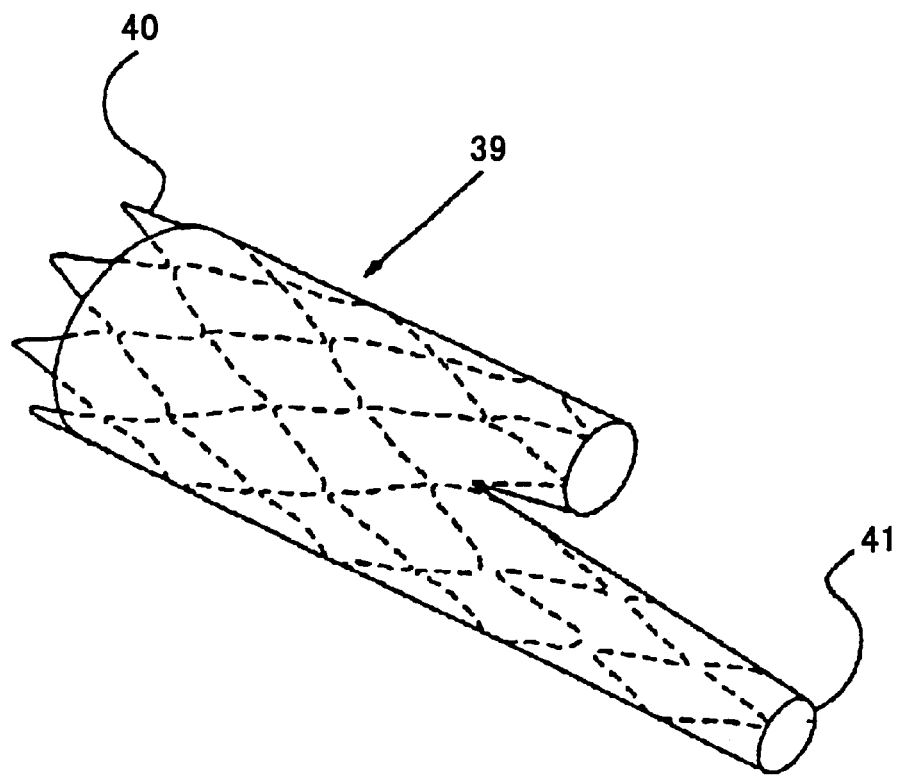
FIG. 11 is perspective view showing further another embodiment of the stent of the present invention.

Stent of FIG. 11 is a tubular member comprising a zigzag β-titanium alloy wire 40 coated with plastic member 41 comprising a good compatibility to living body. As shown in FIG. 11, stent is bifurcated. Stent 39 is inserted into femoral artery through a sheathe for treating aortic aneurysm. Stent 39 has an outer diameter nearly equal to an inner diameter of aorta. Accordingly, stent 39 is shrinked to be contained within the sheathe when inserted through the sheathe. After stent 39 has gone on to aorta through sheathe, the stent 39 will be restored to its original shape due to good elasticity of alloy wire 40 and placed in the main artery.

Since the present invention has the above constitutions, the following effects will be exhibited:

(1) In accordance with the invention as set forth in claim 1, it is possible to provide a method for producing β-titanium alloy wire with a high strength and a good straightness.

(2) In accordance with the invention as set forth in claim 2, the specific aging condition for improving the straightness is proposed.

(3) In accordance with the invention as set forth in claim 3, β-titanium alloy wire can be obtained, which is suitable for metallic wires, such as tension member for communication cable, probe card pin for inspection of conduction, metallic fishing line, wire for medical treatment and the like.

(4) In accordance with the invention, it is possible to provide, β-titanium alloy wire with a high strength and a low Young's modulus suitable for metallic wires, such as tension member for communication cable, probe card pin for inspection of conduction, metallic fishing line and the like.

(5) In accordance with the invention as set forth in claim 5, it is possible to provide a method for producing β-titanium alloy wire with a high strength and a low Young's modulus suitable for metallic wires, such as tension member for communication cable, probe card pin for inspection of conduction, metallic fishing line and the like.

(6) In accordance with the invention, an outer shroud of aluminum or aluminum alloy can prevent the oxide film of β-titanium alloy of center core from being generated and by making good use of ductility of aluminum or aluminum alloy, a good luburicity and a high reduction ratio of area at cold wire-drawing can be achieved. As a result, it is possible to make a reduction ratio over 90% of area at cold wire-drawing and extremely decrease a production cost. Furthermore, since β-titanium and aluminum have a low Young's modulus, Young's modulus of an integrated composite wire becomes low, too. Therefore, β-titanium alloy wire of good ductility can be obtained. This β-titanium alloy wire is suitable for metallic wires necessitating ductility, such as various kinds of precision springs, various kinds of ropes or cables, tension member, metallic fishing line and the like.

(7) In accordance with the invention, it is possible to provide a guide wire for medical treatment with a moderate stiffness and a flexibility by employing β-titanium alloy wire comprising a low Young's modulus and a high strength. Since this guide wire for medical treatment has a center core comprising high elasticity and high strength, a good torque transmittability, a good pushability, a good operationality and a good selectivity at a junction can be achieved.

(8) In accordance with the invention, it is possible to provide a catheter with a moderate stiffness, a flexibility, a good pushability and a crossability by employing β-titanium alloy wire comprising a low Young's modulus and a high strength.

(9) In accordance with the invention, it is possible to provide a stent having a flexibility for passing through the blood vessel and a moderate rigidity after placement to suppress re-stenosis by employing β-titanium alloy wire comprising a low Young's modulus and a high strength.

What is claimed is:

1. A method for producing β-titanium alloy wire comprising the steps of reducing the diameter of β-titanium alloy wire by cold wire drawing followed by heat treatment is characterized in that the heat treatment comprises the first aging process for precipitation strengthening and the second aging process for removing processing strain, and β-titanium alloy wire is heat-treated under the supply of tension at the second aging process.

2. The method for producing β-titanium alloy wire of claim 1, wherein at the second aging process, the temperature is in the range of from 300 to 600° C., the time is in the range of from three minutes to ten minutes and the tension of 0.1 to 30% of breaking load of the β-titanium alloy wire is given to the β-titanium alloy wire.

3. The method for producing β-titanium alloy wire of claim 1, wherein a final diameter of wire is in the range of 0.01 to 2.0 mm.

4. The method for producing β-titanium alloy wire of claim 1, wherein at the first aging process, the temperature is in the range of from 425 to 650° C.

5. A method for production β-titanium alloy wire comprising a diameter of 0.01 to 2.0 mm, said method comprising the steps of subjecting β-titanium alloy wire to solution treatment, coating said β-titanium alloy wire with an oxide film, and giving a reduction ratio of area by cold wire drawing of 70% to 99% to said β-titanium alloy wire in order to provide β-titanium alloy wire having a diameter of 0.01 to 2.0 mm and characterized in that an average crystal grain area A of β-phase in a cross section structure is 1 to 80 μm and a ratio of L/A is 5 to 1000.

* * * * *

UNITED STATES PATENT AND TRADEMARK OFFICE
CERTIFICATE OF CORRECTION

PATENT NO. : 6,800,153 B2
DATED : October 5, 2004
INVENTOR(S) : Naoki Ishii et al.

It is certified that error appears in the above-identified patent and that said Letters Patent is hereby corrected as shown below:

<u>Title page,</u>
Item [30], Foreign Application Priority Data, please insert:
-- Jun. 28 2000  (JP) ................... 2000-200117 --.

Signed and Sealed this

Second Day of August, 2005

JON W. DUDAS
*Director of the United States Patent and Trademark Office*